United States Patent [19]
Andersson et al.

[11] Patent Number: 5,306,830
[45] Date of Patent: Apr. 26, 1994

[54] SUBSTITUTED 3-AMINO CHROMANS

[75] Inventors: Bengt R. Andersson, Lindome; Per A. E. Carlsson, Gothenburg; Kjell A. I. Svensson, Alingsas; Hakan V. Wikstrom, Partille; Anders R. Hallberg, Lund, all of Sweden

[73] Assignee: The Upjohn Company, Kalamazoo, Mich.

[21] Appl. No.: 994,073

[22] Filed: Dec. 21, 1992

Related U.S. Application Data

[63] Continuation of Ser. No. 775,961, Oct. 21, 1991, abandoned, which is a continuation of PCT/US90/01587, Mar. 28, 1990 which is a continuation-in-part of Ser. No. 344,078, Apr. 27, 1989, abandoned.

[51] Int. Cl.$^5$ .......................................... C07D 311/58
[52] U.S. Cl. ............................................................ 549/404
[58] Field of Search ............................................ 549/404

[56] References Cited

U.S. PATENT DOCUMENTS 4,801,605 1/1989 Hutchison .

FOREIGN PATENT DOCUMENTS 87108875 3/1987 Australia .
WO88/04654 6/1988 World Int. Prop. O. .

OTHER PUBLICATIONS

Sarda, N. et al.—Chemical Abstract 85:153938s, "Pharmacological and biochemical study of 3-aminochromans;" (1976).
Sarda, N. et al.—Chemical Abstracts 86:5270y, "Syntheses and conformations of 3-aminochromans," (1977).
Sarda, N. et al.—Chemical Abstract 82:31208w, "Synthesis and stereochemistry of 3-amino-4-chromanols and 3-aminochromans," (1975).
Sarda, N. et al.—Chemical Abstract 92:52486g, "Effects of 3-amino chroman derivatives on the synthesis index, the capture and spontaneous efflux on catecholamines and serotonin in different regions of the rate brain," (1980).
Cossery, J. M. et al.—Chemical Abstract 107:190822t, "The selective labelling of central 5HT$_{1A}$ receptor binding sites by [$^3$H]5-methoxy-d—(di-n-propylamino)-chroman," (1987).

*Primary Examiner*—Nicky Chan
*Attorney, Agent, or Firm*—Donald L. Corneglio

[57] ABSTRACT

The present invention is directed to novel chromane derivatives substituted in the 3-position by a substituted amino moiety and substituted on the aromatic ring with one or two substituents. The novel chromane derivatives have useful CNS properties.

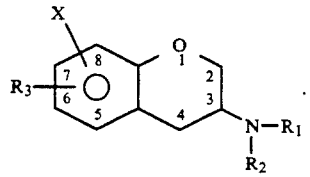

4 Claims, No Drawings

SUBSTITUTED 3-AMINO CHROMANS

This application is a continuation of Ser. No. 07/775,961, filed Oct. 21, 1991, now abandoned, which is a continuation of PCT/US90/01587, filed Mar. 28, 1990, which is a continuation-in-part of Ser. No. 07/344,078, filed Apr. 27, 1989, now abandoned.

FIELD OF THE INVENTION

The present invention is related to novel substituted 3-amino chromans.

BACKGROUND OF THE INVENTION

Evidence from depressed patients indicates the neurotransmission in the central nervous system (CNS) may be disturbed. These disturbances involve the neurotransmitters noradrenaline (NA) and 5-hydroxytryptamine (5-HT). The drugs most frequently used in the treatment of depression are considered to act by improving the neurotransmission of either or both of these physiological agents. The mechanism of action for conventional drugs used to treat mental depression is generally believed to be indirect. It is thought the drugs block the reuptake of the neurotransmitters released from nerve terminals in the CNS, NA and/or 5-HT, which increases the concentration of these transmitters in the synaptic cleft and restores an adequate neurotransmission. For example, the clinically documented antidepression drug, zimelidine (dimethyl-amino-1-(4-bromophenyl)-1-(3-pyridyl)propene) acts as such a reuptake inhibitor with high selectivity for 5-HT neurons.

Available data suggests enhancement of 5-HT neurotransmission will primarily improve depressed mood and anxiety, whereas enhancement of noradrenaline neurotransmission will improve the retardation symptoms occurring in depressed patients. In recent years many efforts have been made to develop new drugs with high selectivity for the improvement of the 5-HT neurotransmission in the CNS.

A fundamentally different way to improve the neurotransmission in the central 5-HT neurons would be to use a 5-HT receptor agonist acting directly upon the 5-HT receptors, and particularly the 5-HT$_{1A}$ receptor. In order to minimize undesired side effects, a high selectivity for this kind of receptor would be necessary.

Clinically, 5-HT$_{1A}$ agonists have also demonstrated anxiolytic properties. The drug, Buspirone, is the only currently available marketed 5-HT$_{1A}$ agonist having anxiolytic activity. This compound antagonizes dopamine receptors at the same dose it stimulates 5-HT$_{1A}$ receptors. These dopamine antagonist properties reduce the clinical utility of these compounds however because long term treatment with dopamine antagonists can produce tardive dyskinesias.

The search for new CNS active compounds is focused on finding compounds with selective 5-HT$_{1A}$ receptor agonist effects without detrimentally influencing central dopamine receptors.

In recent years a large body of pharmacological, biochemical and electrophysical evidence has provided considerable support in favor of the existence of a specific population of central autoregulatory dopamine receptors located in the dopaminergic neuron itself and belonging to the D$_2$ receptor subclass of dopamine receptors. These receptors are part of a homeostatic mechanism that modulates nerve impulse flow and transmitter synthesis and regulates the amount of dopamine released from the nerve endings.

Drugs acting on central dopamine transmission are clinically effective in treating a variety of central nervous system disorders such as parkinsonism and schizophrenia. In parkinsonism, for example, the nigro-neostriatal hypofunction can be restored by an increase in postsynaptic dopamine receptor stimulation. In schizophrenia, the condition can be normalized by achieving a decrease in postsynaptic dopamine receptor stimulation. Classical antipsychotic agents directly block the postsynaptic dopamine receptor. The same effect can be achieved by inhibition of intraneuronal presynaptic events essential for the maintenance of adequate neurotransmission, transport mechanism and transmitter synthesis.

Direct dopamine receptor agonists, like apomorphine, are able to activate the dopamine autoreceptors as well as the postsynaptic dopamine receptors. The effects of autoreceptor stimulation appear to predominate when apomorphine is administered at low doses, whereas at higher doses the attenuation of dopamine transmission is outweighed by the enhancement of postsynaptic receptor stimulation. The antipsychotic and antidyskinetic effects in man of low doses of apomorphine are likely due to the autoreceptor-stimulator properties of this dopamine receptor agonist. This body of knowledge indicates dopamine autoreceptors would be valuable in treating psychiatric disorders.

INFORMATION DISCLOSURE STATEMENT

Ciba-Geigy patent application number EP 222 996 and Astra PCT/SE87/00607 disclose 3-amino substituted chromanes having pharmaceutical activity.

Astra, PCT application WO88/04654, discloses 5-hydroxy, 3-amine chromans which do not include cycloalkyl group substitution of the amine group or halogen substitution at the 8 position.

Sarda, et al., CA 85-153, 938 (1976); CA 86-5270y (1977); CA 82-31208w (1977); CA 82-31208w (1975) and CA, 92-52486 g (1980) discloses various halogen substituted chroman structures although not at the 8 position. Also, described are various hydroxy substituted chromans.

SUMMARY OF THE INVENTION

This invention is to novel chroman compounds of Formula I (see Formula Chart) wherein R$_1$ is H, alkyl C$_{1-3}$ straight or branched, cyclopropylmethyl, or cyclobutylmethyl; R$_2$ is C$_{1-8}$alkyl, —CH$_2$—cycloalkylC$_{3}$–C$_8$, —CH$_2$CH$_2$Z(CH$_2$)$_m$CH$_3$ or —(CH$_2$)$_q$R$_4$ wherein R$_4$ is phenyl; phenyl substituted with one or two substituent groups selected from chlorine, fluorine, bromine, alkylC$_{1-3}$ and alkoxyC$_{1-3}$; 2-thiophene; or 3-thiophene; m is zero to 3; q is 1 to 3; and Z is oxygen or sulfur; R$_3$ is H, SalkylC$_{1-3}$, —S(O)alkylC$_{1-3}$, —S(=O)$_2$alkylC$_{1-3}$, alkoxyC$_{1-8}$, alkenyloxyC$_{3-8}$, —OCH$_2$—cycloalkylC$_{3-8}$ or OH, with the proviso that when R$_3$ is OH or alkoxyC$_{1-8}$, either R$_1$ is cyclopropylmethyl or cyclobutylmethyl or R$_2$ is cycloalkylC$_{3-8}$—CH$_2$—; X is chlorine, fluorine, bromine, CF$_3$, —NR$_5$R$_6$, —NR$_7$C(=O)R$_8$, —NR$_9$C(=O)R$_{10}$, or —NR$_{11}$C(=O)NR$_{12}$R$_{13}$ wherein R$_2$, R$_6$, R$_7$, R$_9$, R$_{11}$, R$_{12}$ and R$_{13}$ are H or alkylC$_{1-5}$ or —NR$_5$R$_6$ taken together form a monocyclic heterocyclic selected from pyrrolidino, piperidino, N-methylpiperazino, or morpholino; R$_8$ is H or alkylC$_{1-5}$; and R$_{10}$ is alkylC$_{1-5}$ or —(CH$_2$)$_n$—phenyl wherein n is zero to two; and pharmaceutically acceptable salts thereof.

Preferably, when X is F, Cl, Br or $NH_2$, X is at the number eight carbon position.

The compounds of this invention possess selective pharmacological properties and are useful in treating central nervous system disorders including depression symptoms, anxiety symptoms, panic attacks, obsessive-compulsive disturbances, senile dementia, emotional disturbances related to dementia disorders, and disturbances of sexual functions. The compounds of this invention are also useful to alleviate aggressive behavior, confusional delirious states and impotence.

According to a preferred embodiment, the invention is related to compounds of Formula I where $R_2$ is $—CH_2—$cycloalkyl$(C_{3-8})$. A more preferred embodiment are compounds of Formula I where $R_1$ is alkyl(C$_{1-5}$ $R_3$), $R_2$ is cyclopropylmethyl, and $X_1$ is halogen.

An object of the invention is to provide compounds for therapeutic use, especially compounds having a therapeutic activity in the central nervous system. Another object is to provide compounds having an effect on the 5-$HT_{1A}$ receptor in mammals including man. A further object of this invention is to provide compounds having an effect on the subclass of dopamine receptors known as the $D_2$ receptor.

DETAILED DESCRIPTION OF THE INVENTION

The compounds of this invention are identified in two ways: by the descriptive name and reference to labelled structures contained in Formula Charts.

As used herein the parenthetical term $(C_n-C_m)$ is inclusive such that a compound of $(C_{1-8})$ would include compounds of one to 8 carbons and their isomeric forms. The various carbon moieties are defined as follows: Alkyl refers to an aliphatic hydrocarbon chain and includes branched or unbranched forms such as methyl, ethyl, n-propyl, isopropyl, n-butyl, isobutyl, sec-butyl, t-butyl, n-pentyl, isopentyl, neo-pentyl, n-hexyl, isohexyl, n-heptyl, isoheptyl, and n-octyl. Alkoxy refers to an alkyl which is attached to the remainder of the molecule by oxygen and includes branched or unbranched forms such as methoxy, ethoxy, n-propoxy, isopropoxy, n-butoxy, isobutoxy, sec-butoxy, t-butoxy, n-pentoxy, isopentoxy, neo-pentoxy, n-hexoxy, isohexoxy, n-heptoxy, isoheptoxy, and n-octoxy. Alkenyloxy refers to an aliphatic unsaturated hydrocarbons having a double bond and which is attached to the remainder of the molecule by oxygen and includes both branched and unbranched forms such as 1-propenyloxy, 2-propenyloxy, 1-butenyloxy, 2-butenyloxy, 3-butenyloxy, 2-methyl-1-butenyloxy, 1-pentenyloxy, 2-pentenyloxy, 3-pentenyloxy, 4-pentenyloxy, 1-methyl-4-pentenyloxy, 3-methyl-1-pentenyloxy, 3-methyl-2-pentenyloxy, 1-hexenyloxy, 2-hexenyloxy, 3-hexenyloxy, 4-hexenyloxy, 1-methyl-4-hexenyloxy, 3-methyl-1-hexenyloxy, 3-methyl-2-hexenyloxy, 1-heptenyloxy, 2-heptenyloxy, 3-heptenyloxy, 4-heptenyloxy, 1-methyl-4-heptenyloxy, 3-methyl-1-heptenyloxy, 3-methyl-2-heptenyloxy, 1-octenyloxy, 2-octenyloxy, or 3-octenyloxy. Cycloalkyl refers to a saturated cyclic hydrocarbon such as cyclopropyl, cyclobutyl, cyclopentyl, cyclohexyl, cycloheptyl, or cyclooctyl. The group Salkyl$C_1-C_3$ is representative of methylthio, ethylthio and propylthio substituent groups.

It will be apparent to those skilled in the art that compounds of this invention may contain chiral centers. The compounds of Formula I contain asymmetric carbon atoms in the aliphatic ring moiety, including the ring carbon atoms adjacent to the nitrogen atom. The therapeutic properties of the compounds may to a greater or lesser degree depend on the stereochemistry of a particular compound. The scope of this invention includes all enantiomeric or diastereomeric forms of Formula I compounds either in pure form or as mixtures of enantiomers or diastereomers. Pure enantiomers as well as enantiomeric or diastereomeric mixtures are within the scope of the invention.

The X substituent of Formula I is shown in between carbon atoms 7 and 8 indicating it can be substituted at either of these positions unless otherwise indicated. Preferably, X is positioned at the 8 carbon atom.

The $R_3$ substituent of Formula I is shown between carbon atoms 6 and 7 which indicates it can be present at any of carbon atoms 5, 6 or 7. The preferred substituted carbon atom is number 6 and, of course, number 7 is not available when "X" is substituted at this position.

Both organic and inorganic acids can be employed to form non-toxic pharmaceutically acceptable acid addition salts of the compounds of this invention. Illustrative acids are sulfuric, nitric, phosphoric, hydrochloric, citric, acetic, lactic, tartaric, pamoic, ethanedisulfonic, sulfamic, succinic, cyclohexylsulfamic, fumaric, maleic, and benzoic acid. These salts are readily prepared by methods known in the art.

A pure enantiomer of a compound of Formula I may be prepared by converting the secondary amine of an appropriate final product of Formula I or an intermediate thereto as described in Chart I or as set forth in the Formula Chart into the (−)-O-methylmandelic acid. amide followed by chromatographic separation of the two diastereomers and cleavage by subsequent reaction with potassium tert-butoxide in tetrahydrofuran with traces of water and methyl lithium. In the case of an incomplete reaction, the intermediate N-formyl derivative can be cleaved by the addition of methyl lithium to an ether solution of the formancide and subsequently quench with water and ether extraction to give the secondary amine. The secondary amine can be converted into the tertiary amine using methods already described.

In clinical practice the compounds of the present invention will normally be administered orally, rectally, or by injection, in the form of pharmaceutical preparations comprising the active ingredient either as a free base or as a pharmaceutically acceptable non-toxic, acid addition salt, such as the hydrochloride, lactate, acetate, sulfamate salt, in association with a pharmaceutically acceptable carrier. The use and administration to a patient to be treated in the clinic would be readily apparent to a person of ordinary skill in the art.

In therapeutic treatment the suitable daily doses of the compounds of the invention are 1-2000 mg for oral application, preferentially 50-500 mg, and 0.1-100 mg for parenteral application, preferentially 0.5-50 mg. The daily dosage will preferably be administered in divided dosages one to 4 times daily and the dosage amounts are based on an individual having a weight of about 70 kg.

The compounds of this invention where $R_2$ is cycloalkylmethyl also have high oral potency and a long duration of action. Both these features are beneficial to effective clinical treatment.

The utility of the compounds of this invention to treat central nervous system disorders is shown in behavioral and biochemical activity in reserpine-pretreated rats.

Depletion of CNS monoamine stores with reserpine brings about a "neuroleptic syndrome" characterized by hypomotility, catalepsy, muscle rigidity, hunchbacked posture as well as a number of other central and peripheral signs of monoamine depletion. The whole or parts of this syndrome can be reversed by the administration of drugs that stimulate DA or 5-HT receptors directly or indirectly.

Stimulation of the DA receptors, with apomorphine for example, gives rise to both locomotion and stereotyped behavior such as sniffing, gnawing and jumping. On the other hand, stimulation of the 5-HT receptors, with 5-hydroxytryptophan (5-HTP) combined with MAO-inhibitors for example, gives rise to a very different behavior. The animals lie flat on the cage floor exhibiting forward movements with extended forepaws padding, "piano-playing," and abducted hindlegs, occasionally with some tremor in the forebody and with Staubtail, stiff tail erection.

The compounds under evaluation are tested biochemically for central DA- and 5-HT receptor (pre- and/or postsynaptic) stimulating activity. The concept of this biochemical screening method is that a DA- or 5-HT-receptor agonist will stimulate the receptor and through regulatory feedback systems effect a decline in tyrosine or tryptophan hydroxylating activity, respectively, and a subsequent reduction in the synthesis rate for DA and 5-HT in the presynaptic neuron. Dopa and 5-HTP formation, as determined after in-vivo inhibition of the aromatic L-amino acid decarboxylase with NSD 1015 (3-hydroxybenzylhydrazine hydrochloride) are taken as indirect measures of DA- and 5-HT-synthesis rates, respectively as described by H. Wikstrom, et al., J. Med. Chem. 27, 1030 (1984).

The compounds of this invention are prepared by various means. The compounds of this invention wherein $R_3$ is hydrogen, $R_1$ is hydrogen, ethyl or propyl, cyclopropylmethyl or cyclobutylmethyl and $R_2$ is —$CH_2$cycloalkyl$C_{3-8}$, alkyl$C_{2-8}$, —$(CH_2)_q$—$R_4$, or —$CH_2CH_2O(CH_2)_rCH_3$ are prepared by refluxing one equivalent of a salicyl aldehyde of formula C-1 (see Chart 1) with one and one-half equivalents of 2-nitroethanol in amylacetate in the presence of one and one-half equivalents of din-propylamine hydrochloride followed by azeotropic distillation for 12 hours in a Dean-Stark apparatus to give the 3-nitrochromene of formula C-3. The 3-nitrochromene is reduced with cyanoborohydride or zinc and HCl to give the 3-aminochromane of C-4. The 3-aminochromane of C-4 can be acylated with an appropriate acid halide, e.g., acid chloride, of the formula $R_yCO$halide wherein $R_y$ is alkyl$C_{1-7}$, —$(CH_2)_tR_4$ wherein t is 1 or 2, cycloalkyl$C_{3-8}$ or —$CH_2O(CH_2)_mCH_3$ wherein $R_5$ and m have the meanings in Formula I to give the chromane amides of formula C-5. Also the aminochromane of formula C-4 can be treated with methyl iodide to give the compound of formula C-6 wherein $R_{14}$ is hydrogen and $R_{15}$ is methyl or can be treated with formaldehyde in water in the presence of NaBH$_3$CN and a few drops of glacial acetic acid at pH5 to give the corresponding dimethylated compounds. The compounds of formulas C-5 and C-6 can be converted to the corresponding compounds of formulas C-7 and C-8 wherein R is F, Cl, CF$_3$, NR$_5$R$_6$, NR$_7$C(=O)R$_8$, NR$_9$C(=O)OR$_{10}$, or NR$_{11}$C(=O)NR$_{12}$R$_{13}$ as follows:

(1) The compounds of C-5 and C-6 can be treated with sodium trifluoroacetate and copper iodide in DMPU at 160° C. for four hours under argon to give C-7 and C-8 compounds wherein R is CF$_3$.

(2) Compounds of C-5 and C-6 can be treated with n-butyllithium in THF or ether letting the reaction begin at −78° C. using carbon dioxide/ice mixture, quenching the reaction at 0° C. and then letting the reaction mixture warm to room temperature to give the compounds of C-7 and C-8 wherein R is lithium.

(3) The lithiated compounds can be treated with methoxylamine to give the corresponding amine, i.e., compounds of C-7 and C-8 wherein R is NH$_2$.

(4) The C-7 and C-8 compounds wherein R is NH$_2$ can be diazotized using diazonium hexafluorophosphate by procedures well known in the art to give the corresponding C-7 and C-8 compounds wherein R is fluoro.

(5) The C-7 and C-8 compounds wherein R is NH$_2$ also can be converted to the corresponding compounds wherein R is Cl by the well known Sandmeyer reaction. Additionally the C-7 and C-8 compounds can be converted to the corresponding compounds wherein R is NR$_5$R$_6$, NR$_7$C(=O)R$_8$, NR$_9$C(=O)OR$_{10}$ or NR$_{11}$C(=O)NR$_{12}$R$_{13}$ as follows. To prepare compounds of formula C-5 wherein R is NR$_5$R$_6$ the corresponding amine substituted compound is alkylated using an appropriate alkyl halide. C-5 compounds wherein R is NHC(=O)R$_8$ are prepared by acylating the corresponding amine substituted compound with a compound of the formula R$_8$COCl in methylenechloride in the presence of triethylamine. Alternatively, one could use a mixed anhydride reaction. Compounds of formula C-5 wherein R is NHC(=O)OR$_{10}$ can be prepared from the corresponding amine substituted compounds by treatment with phosgene or 1,1'-carbonyldiimidazole to give the corresponding carbamoylchloride which is treated with an alcohol or phenol of the formula R$_{10}$-OH to give the desired carbamate. The compounds of C-5 wherein R$_6$ is NHC(=O)NR$_{12}$R$_{13}$ are prepared from the corresponding amine substituted compounds by treatment with a suitable carbamoyl chloride of the formula R$_{12}$R$_{13}$NCOCl in the presence of triethylamine, or by treatment of the above described carbamoyl chloride with a suitable amine of the formula R$_{12}$R$_{13}$NH in the presence of triethylamine. The corresponding compounds wherein R$_7$, R$_9$ or R$_{11}$ is alkyl are obtained by alkylation with an appropriate alkyl halide.

The compounds of C-6 and the compounds of C-8 wherein R is as defined above excepting lithium are final products of the invention. The compounds of formula C-7 wherein R is other than lithium and the compounds of C-5 can be converted to final products of the invention, as represented by compounds of formula C-9 wherein R$_{16}$ is alkyl$C_{2-8}$, $(CH_2)_qR_4$, —CH$_2$cycloalkyl$C_{3-8}$, or —CH$_2$CH$_3$O(CH$_2$)$_r$CH$_3$ by mixed hydride reduction using, e.g., lithium aluminum hydride in ether or tetrahydrofuran, sodium borohydride in acetic or trifluoroacetic acid, diborane in THF or QBH$_4$ in a mixture of dichloromethane and dichloroethane wherein Q represents tetrabutylammonium ion. The reagent QBH$_4$ is especially preferred when the amide compound is substituted on the aromatic ring with halogen and in particular bromine. The compounds of C-9 can also be used to prepare other compounds of the invention as represented by the compounds of C-11 wherein R$_{16}$ is as defined above and R$_{17}$ is alkyl$C_{2-3}$, cyclopropylmethyl or cyclobutylmethyl by treating the C-9 compounds with an appropriate acid halide of the formula R$_x$CO halide wherein R$_x$ is methyl, ethyl, cyclobutylmethyl or cyclopropylmethyl to give the C-10 intermediate amide which is subjected to mixed hydride reduction as described above to give the C-11 compounds.

To prepare compounds of this invention wherein $R_3$ is -Salkyl$C_{1-3}$ the appropriate compounds of C-7 and C-8 wherein R is lithium as described above are treated with an appropriate alkyl disulfide of the formula alkyl$C_{1-3}$SSalkyl$C_{1-3}$ to give compounds of formulas C-12 and C-13 respectively (see Formula Chart) wherein $R_y$, $R_{14}$ and $R_{15}$ are as defined hereinabove. The compounds of formulas C-12 and C-13 can be treated in the same manner as described hereinabove for compounds of formulas C-5, C-6, C-7, C-8, C-9 and C-10 to give compounds of formula C-14 wherein X has the meaning defined in Formula I, $R_{18}$ is H, alkyl$C_{1-3}$, cyclopropylmethyl or cyclobutylmethyl, and $R_{19}$ is alkyl$C_{1-8}$, —(CH$_2$)$_q$—$R_4$, —CH$_2$cycloalkyl$C_{3-8}$ or —CH$_2$CH$_2$O(CH$_2$)$_m$CH$_3$ wherein q, m, and $R_4$ are as defined in Formula I. The sulfone and sulfoxide derivatives, i.e., compounds of formula I wherein R3 is —S(O)alkyl$C_{1-3}$ or —S($=$O)$_2$alkyl$C_{1-3}$ are prepared from the alkyl$C_{1-3}$-thio compounds by oxidation with m-chloroperbenzoic acid by procedures well known in the art.

The compounds of this invention wherein $R_3$ is OH can be prepared from the compounds of C-7 and C-8 wherein R is lithium by quenching the lithiated compound in nitrobenzene to give the compounds of formula C-15 and C-16. The compounds of C-15 and C-16 are then treated with BR$_2$ dissolved in methylene chloride to give the compounds of formulas C-17 and C-18. After suitably protecting the OH group in the compounds of formulas C-17 and C-18 said compounds can be treated in the same manner as described hereinabove for compounds of formulas C-5, C-6, C-7, C-8, C-9 and C-10 and followed by removal of the hydroxy protecting group to give compounds of formula C-19 wherein X has the meaning defined in Formula I and $R_{18}$ and $R_{19}$ have the meanings defined in formula C-14. The compounds of C-19 can be converted to the compounds of Formula I wherein $R_3$ is alkoxy $C_{1-8}$, alkenyloxy$C_{3-8}$ or —OCH$_2$cycloalkyl$C_{3-8}$ by treatment with an alkyl halide or tosylate $R_bX$ wherein $R_b$ is alkyl$C_{1-8}$, alkenyl$C_{3-8}$, or —CH$_2$cycloalkyl$C_{3-8}$ and X or the halide is Cl, Br, I or T$_s$O in an organic solvent such as acetonitrile or acetone and in the presence of a base such as potassium carbonate or sodium hydroxide.

The compounds of this invention wherein $R_2$ is —CH$_2$CH$_2$S(CH$_2$)$_r$CH$_3$ can be obtained by reacting a ketone of formula C-20 with an alkylthiaalkylamine of the formula H$_2$NCH$_2$CH$_2$S(CH$_2$)$_r$CH$_3$ wherein r is zero to 3 in the presence of NaBH$_3$CN to give compounds of formula C-21 which can be treated with an appropriate acyl halide to give compounds of Formula I wherein $R_1$ is alkyl$C_{1-3}$, cyclopropylmethyl or cyclobutylmethyl. The various X and $R_3$ substituent groups on the aromatic ring of the compounds of Formula I can be obtained generally as described hereinabove. For example, a compound of C-21 could be converted to the corresponding hydroxy substituted compound which then could be alkylated to give the various alkoxy, alkenyloxy and cycloalkylmethoxy derivatives. Similarly other final products can be obtained by conversion of the aromatic substituent groups as generally described hereinabove.

The following detailed examples describe how to prepare the various compounds and/or perform the various processes of the invention and are to be construed as merely illustrative, and not limitations of the preceding disclosure in any way whatsoever. Those skilled in the art will recognize appropriate variations from the procedures both as to reactants and as to reaction conditions and techniques.

EXAMPLE 1

Preparation of Intermediate 6-Bromo-3-(di-n-propylamino)chromane

The free base of 3-(di-n-propylamino)chromane (60 mg, 0.026 mmol) was converted to the hydrochloride with HCl-saturated EtOH. The residue after evaporation of the solvent and excess HCl was dissolved in CH$_2$Cl$_2$ and 4 equivalents of Br$_2$ dissolved in CH$_2$Cl$_2$ were added. The reaction was complete after 2 hours and water was added. The product was found in the organic layer, which was basified with 10% Na$_2$CO$_3$. The organic phase was dried (Na$_2$SO$_4$), filtered and the solvent was evaporated, yielding an oil, which was converted to the hydrochloride with HCl-saturated EtOH. Crystals were formed from EtOAc-Hexane (30 mg) melting at 120° C. GC/MS showed M+/M+2 at m/e=310.95(10%)/312.95(10%) and the base peak pair at m/e=282.00(100%)/284.00(97%).

EXAMPLE 2

Preparation of Intermediate 8-Bromo-3-chromanol

Tl$_2$O$_3$ (2.38 g, 5.2 mmol) was added at room temperature to a mixture of H$_2$SO$_4$ (6.9 ml) and water (6.1 ml) and this mixture was stirred for 30 min and added to o-allyloxy-bromo-benzene (1.9 g, 8.92 mmol) and water was added (37 ml). The reaction mixture was stirred in 60° C. under Argon. The product was extracted with CH$_2$Cl$_2$ and the organic layer was washed with water, dried (Na$_2$SO$_4$), filtered and the solvent was removed under reduced pressure to give 1.34 g of a raw oil, which was chromatographed (SiO$_2$ and ether as eluant). The fractions containing at least 85% purity of the product were pooled and the solvent was removed, yielding 310 mg of an oil. GC/MS showed M+/M+2 at m/e=228.00(100%)/230.00(88%).

EXAMPLE 3

Preparation of Intermediate 8-Bromo-3-chromanone

The 8-bromo-3-chromanol was oxidized in small portions (400 mg, 1.7 mmol) in order to achieve better total yields. Dry pyridine (1.1 ml) was added to CH$_2$Cl$_2$ (60 ml), dried over P$_2$O$_5$ and CrO$_3$ (0.69 g, 6.9 mmol) and molecular sieves were added to that solution. After 15 min the chromanol was added together with acetic anhydride (0.66 ml). The mixture was stirred for 10 min and then passed with suction through a column containing SiO$_2$ (10 g), eluting with CH$_2$Cl$_2$. The collected eluate was evaporated and toluene was added after each evaporation (2-3 times), leaving the pure 8-bromo-3-chromanone (200 mg). GC/MS showed M+/M+2 at m/e=226.25(89%)/228.25(82%).

EXAMPLE 4

8-Bromo-3-(di-n-propylamino)chromane

8-Bromo-3-chromanol (80% according to GC, 0.8×0.69 g, 0.8×3.0=2.4 mmol) was dissolved in dry benzene and di-n-propylamine (2 ml) and p-toluenesulfonic acid (60 mg) was added. The reaction mixture was refluxed under N$_2$ and water separation in a Dean-Stark apparatus. The solvents were removed under reduced pressure and the residue was dissolved in MeOH (50 ml)

and NaBH₃CN (2.0 g) was added and the mixture was stirred overnight. Water (50 ml) and 15% NaOH (5 ml) was added and the product was extracted to CH₂Cl₂. The organic layer was washed with water, dried (Na₂SO₄), filtered and the solvents were removed under reduced pressure, leaving 700 mg of the raw product, which was chromatographed (SiO₂, 100 g) using petroleum ether:ether (9:1) as the eluant. The fractions containing pure product were pooled and the solvent was evaporated. The residual oil was converted into the hydrochloride with HCl-saturated EtOH. Crystals (248 mg) melting at 135° C. were obtained from EtOAc/ether. GC/MS showed M+/M+2 at m/e=311.05(7.7%)/313.05(8.7%) and the base peak pair at m/e=281.95(98%)/283.95(100%).

EXAMPLE 5

Preparation of Intermediate 5-Methoxy-3-chromanol and 7-methoxy-3-chromanol

To a mixture of H₂SO₄ (50 ml) and water (58 ml) at room temperature, Tl₂O₃ (20.4 g, 44.7 mmol) was added. The mixture was stirred for 30 min and then another portion of water (350 ml) was added. The temperature was raised to 60° C. and 3-allyloxyanisol synthesized by known methods (14.6 g, 90.0 mmol) was added. The mixture was stirred for 16 hours. Another portion of Tl₂O₃ (10.2 g, 22.3 mmol) stirred for 30 min at 20° C. in H₂SO₄ (25 ml) and water (30 ml) was added and the reaction mixture was stirred for another 12 hours at 60° C. The mixture was extracted after cooling with chloroform. The organic layer was washed with water, dried (MgSO₄) and the solvent was evaporated. The crude product was chromatographed (SiO₂) with ether as eluant. The 7-methoxy isomer eluted first as a pure product according to GC-analyses.

The fractions containing enriched 5-methoxy isomer were further chromatographed (SiO₂) with light petroleum ether (1:1) as eluant affording pure 5- and 7-methoxy isomers. The yields of these isomers were 1.16 g (8%) and 3.19 g (22%), respectively. Analytic samples of these isomers were obtained after recrystallization in light petroleum ether.

The 5-methoxy isomer could alternatively be synthesized from 8-bromo-5-methoxy-3-chromanol (400 mg, 1.54 mmol) with catalytic hydrogenation (Pd/C) overnight in ethanol with 5N-NaOH solution in 90% yield.

Analytical data of 5-methoxy-3-chromanol: m.p. 96-98. ¹H NMR (CDCl₃) δ 2.1-2.4 (s,br,1H), 2.7-2.8 (d,d,1H), 2.8-2.9 (d,d,1H), 3.8 (s,3H), 4.0-4.1 (s,br,2H), 4.2-4.3 (m,1H), 6.4 (d,1H), 6.5 (d,1H), 7.0-7.1 (t,1H). ¹³C NMR δ 28.40, 55.44, 62.98, 69.30, 102.53, 108.58, 109.31, 127.26, 154.60, 158.49. GC/MS (HP-5970A) m/e=180 (93)M+, 136 (100), 106 (44), 137 (23), 108 (22).

Analytical data of 7-methoxy-3-chromanol: m.p. 62°-64° C. ¹H NMR (CDCL₃) δ 1.95-2.0 (s,br,1H), 2.65-2.75 (d,d,1H), 2.25-3.10 (d,d,1H), 3.7 (s,3H), 4.0-4.1 (m,2H), 4.15-4.25 (m,1H), 6.4 (d,1H), 6.5 (d,d,1H), 6.95 (d,1H). ¹³C NMR δ 32.94, 51.31, 63.40, 69.75, 101.52, 108.10, 111.23, 130.86, 154.49, 159.34. GC/MS (HP-5970A) m/e=180 (78) M+, 136 (100), 137 (79), 108 (61), 78 (28).

EXAMPLE 6

Preparation of Intermediate 3-Allyloxy-4-bromoanisol

To a solution of 4-bromo-3-hydroxyanisol (14.49, 59.3 mmol), synthesized by known methods, in CH₃CN (200 ml), dry potassium carbonate (20 g) and allylbromide (8.0 ml, 92.4 mmol) was added. The reaction mixture was stirred and refluxed for 1 hour and thereafter cooled to room temperature, filtered and evaporated. The residue was dissolved in ether and extracted with water. The organic layer was separated and dried (Na₂SO₄). Evaporation of the solvent afforded 16.0 g (93%) of 3-allyloxy-4-bromoanisol as an oil. GC/MS (HP-5970A) m/e=244 (40) M+ and M+ −1 at m/e=242 (40), 163 (100), 149 (97), 135 (62).

EXAMPLE 7

Preparation of Intermediate 8-Bromo-5-methoxy-3-chromanol

To a mixture of H₂SO₄ (6.9 ml) and water (6.1 ml) at room temperature was added Tl₂O₃ (2.38 g, 5.22 mmol). The mixture was stirred for 30 min and water (37 ml) was added, thereafter the temperature was raised to 60° C. and 3-allyloxy-4-bromoanisol (2.16 g, 8.89 mmol) was added. The mixture was stirred at 60° C. for 4.5 hours. Another portion of Tl₂O₃ (1.0 g, 2.19 mmol) stirred for 30 min at 20° C. in H₂SO₄ (2.6 ml) and H₂O (3 ml) was added and the reaction mixture was stirred for another 17 hours at 60° C. After cooling the mixture was extracted with chloroform. The organic layer was washed with water, dried (MgSO₄) and evaporated. After chromatography (SlO₂) with ether as eluant, 552 mg (24%) of 8-bromo-5-methoxy-3-chromanol was isolated. An analytic sample of the product was obtained from recrystallization in light petroleum-ether, m.p. 115°-117° C.

¹H NMR (CDCl₃) δ 2.0-2.1 (s,br,1H), 2.7-2.8 (d,d,1H), 2.9-3.0 (d,d,1H), 4.1 (s,3H), 4.8-5.0 (m,3H), 6.4 (d,1H), 7.3 (d,1H). ¹³C NMR δ 28.65, 55.64, 62.64, 70.08, 101.85, 103.79, 110.34, 130.49, 150.75, 157.70. GC/MS (HP-5970A), m/e=260 (99) M+1, 258 (100) M−1, 216 (93), 214 (91), 185 (50).

EXAMPLE 8

Preparation of Intermediate 8-Bromo-5-methoxy-3-chromanone

To a solution consisting of dry pyridine and CH₂Cl₂ (120 ml, dried over P₂O₅) CrO₃ (435 mg, 4.35 mmol) was added. The mixture was stirred for 15 min and 8-bromo-5-methoxy-3-chromanol (293 mg, 1.13 mmol) was dissolved in 10 ml dry CH₂Cl₂ was added and immediately thereafter acetic acid anhydride (0.41 ml, 4.35 mmol) was added to the solution. The mixture was stirred for 10 min and then sucked through a short silica column (13 g SiO₂) with vacuum. The column was washed with CH₂Cl₂ and the solvent evaporated yielding 237 mg (81%) of the product. An analytic sample was obtained from recrystallization in light petroleum-ether, m.p. 97°-100° C. ¹H NMR (CHCl₃) δ 3.55 (s,2H), 3.80 (s,3H), 4.45 (s,2H), 6.5 (d,1H), 7.4 (d,1H). GC/M (HP-5970A) m/e=258 (64) M+1, 256 (57) M−1, 134 (100), 50 (11), 76 (11).

EXAMPLE 9

Preparation of Intermediate 5-Methoxy-3-chromanone

5-Methoxy-3-chromanone was obtained from oxidation of 5-methoxy-3-chromanol (2.5mmol) analogously with the synthesis of 8-bromo-5-methoxy-3-chromanone above in 62% yield. GC/MS (HP-5970A), m/e-178 (100) M+, 177 (83), 135 (20), 43 (22), 91 (18).

EXAMPLE 10

Preparation of Intermediate
8-Bromo-3-(di-n-propylamino)-5-methoxychroman

To a solution of 8-bromo-5-methoxy-3-chromanone (550 mg, 2.14 mmol) in benzene (40 ml), di-n-propylamino (1.8 ml, 13.2 mmol) and p-toluenesulfonic acid, monohydrate (41 mg, 0.32 mmol) was added. The solution was refluxed for 5 hours with a Dean-Stark apparatus under nitrogen atmosphere. After cooling to room temperature a solution of sodium cyanoborohydride (2.0 g, 32 mmol) dissolved in MeOH (50 ml) was added and thereafter stirred overnight. Water was added (50 ml) and 5% NaOH-solution (5ml). The solution was extracted with $CH_2Cl_2$. The organic layer was separated, washed with water and dried ($Na_2SO_4$). The solvent was evaporated and the residue was chromatographed ($SiO_2$) with light petroleum-ether (3:1) as eluant yielding 550 mg (75%) as an oil. The amine was converted to its hydrochloride with HCl-saturated ethanol. Evaporation and recrysstallization (ethanol-ether) gave the product as crystals.

m.p. 180°–182° C. $^1$H NMRA ($CDCl_3$) 0.6–0.9 (t,6H), 1.1–1.6 (m,4H), 2.5–3.3 (m,8H), 3.75 (s,3H), 4.2–4.5 (m,1H), 6.25–6.35 (d,1H), 7.2–7.4 (d,1H). GC/MS (HP-5970A), m/e=343 (10) M+1, 341 (10), M−1, 312 (100), 314 (91), 241 (80).

Anal. ($C_{16}H_{25}BrNO_2Cl$) Calcd. C 50.7, H 6.7, N 3.7. Found C 50.2, H 6.6, N 3.5.

EXAMPLE 11

Preparation of Intermediate
3-(Di-n-propylamino)-5-methoxychroman

To a solution of 8-bromo-5-methoxy-3-chromanone (125 mg, 0.49 mmol) in benzene (20 ml) was added di-n-propylamine (0.5 ml, 3.7 mmol) and p-toluenesulfonic acid monohydrate (10 mg, 0.08 mmol). The solution was refluxed for 5 hours with a Dean-Stark apparatus under $N_2$-atmosphere. The reaction mixture was poured into a Parr-flask, absolute ethanol was added (50 ml) and pH was adjusted to 11 with 2M-NaOH-solution. The product was hydrogenated overnight with Pd/C as catalyst. The catalysst was filtered off and the solvent was evaporated. The residual oil was dissolved in $CH_2Cl_2$ and washed with 5% aqueous $Na_2CO_3$. The phases were separated and the organic layer was dried ($Na_2CO_3$) yielding 99 mg (77%) of the product as an oil with physical data identical with authentic material synthesized by alternative methods.

EXAMPLE 12

Preparation of Intermediate
5-Methoxy-8-methylthio-3-(di-n-propylamino)chroman

A solution of 8-bromo-5-methoxy-3-(di-n-propylamino)chromane (174 mg, 0.51 mmol) in dry ether was treated with 1.6 M-n-BuLi in hexane (0.6 ml, 0.96 mmol) at 0° C. for 30 min under dry Ar-atmosphere. Dry, distilled methyl disulfide was added (0.2 ml, 2.3 mmol) and the mixture was stirred for 2 hours at 0° C. and was then allowed to reach room temperature. Water was added and the phases were separated. The organic layer was washed with water, separated and dried ($Na_2SO_4$). The solvent was evaporated and the remaining oil chromatographed ($SiO_2$) with light petroleum-ether (3:1) as eluant yielding 105 mg (67%) of the product as an oil. The amine was converted to its hydrochloride with HCl-saturated ethanol. Evaporation and recrystallization from light petroleum-ether gave the product as crystals.

m.p. 138°–140° C. $^1$H NMR ($CDCl_3$) δ 0.7–1.1 (t,6H) 1.2–1.7 (m,4H), 2.4 (s,3H), 2.4g–3.40 (m,8H), 3.9 (s,3H), 4.4–4.6 (m,1H) 6.45–6.55 (d,1H), 7.15–7.30 (d,1H). GC/MS (HP-5970A), m/e=309 (41) M+, 209 (100), 280 (99), 162 (26), 281 (19).

Anal. ($C_{17}H_{28}NO_2SCl$) Calc. C 59.0, N 8.2, H 4.1. Found C 58.5, N 8.3, H 4.0.

EXAMPLE 13

Preparation of Intermediate
5-Methoxy-3-(N-methylthioethyl-N-propionylamino)-chroman To a solution of the appropriate amine (400 mg, 2.27 mmol) and acetic acid (400 mg, 6.99 mmol) in absolute ethanol (10 ml) was added 5-methoxy-3-chromanone (250 mg, 1.40 mmol), followed by 2-methylthioethylamine (0.6 ml, 6.41 mmol). The solution was stirred with 4 Å molecular sieve for 1 hour 15 min. MeOH (25 ml) was added to the reaction mixture and sodium cyanoborohydride (1.5 g, 23.6 mmol) dissolved in MeOH (10 ml). The reaction mixture was stirred for 30 min, water was added (50 ml) and pH adjusted with 5% aqueous NaOH to 11. The mixture was extracted with $CH_2Cl_2$. The phases were separated and the organic layer washed with water, dried ($Na_2SO_4$) and the solvent was evaporated. The crude product was immediately propionylated with propionyl chloride (0.5 ml, 5.72 mmol) in $CH_2Cl_2$ (20 ml) containing triethylamine (1 ml, 7.2 mmol). The reaction mixture was stirred for 30 min, washed with aqueous sodium carbonate solution, 1N HCl and water. The organic layer was separated and dried ($MgSO_4$). The solvent was evaporated and the crude product chromatographed ($SiO_2$) with light petroleum-ether (1:1) as eluant yielding 276 mg (64%) of the product as an oil. GC/MS (HP-5970A), m/e=310 (0.2) M+, 162 (100), 161 (54), 163 (50), 192 (22).

High resolution MS with FAB ionisation showed M+ at m/e 311.141±10 ppm. (Calc 311.157).

$^1$H NMR ($CDCl_3$) δ 1.1–1.3 (t,3H), 1.90–3.05 (m,9H), 3.30–3.65 (m,2H), 3.85 (s,3H), 4.05–4.40 (t,br,2H), 4.5–4.8 (s,br,1H), 6.4–6.7 (d,d,2H), 7.05–7.3 (t,1H).

EXAMPLE 14

Preparation of Intermediate
5-Methoxy-3-(N-methylthioethyl-N-n-propylamino)-chroman A solution of 5-methoxy-3-(N-methylthioethyl-N-propionylamino)chroman (207 mg, 0.70 mmol) in dry ether (10 ml) was cooled with ice and $LiAlH_4$ (250 mg, 6.59 mmol) was added. The mixture was stirred at 0° C. for 40 min. Usual workup gave 195 mg (99%) of the amine as an oil. GC/MS (HP-5970A), at m/e=295 (0.1) M+, 163 (100), 234 (98), 235 (15), 164 (10).

High resolution MS with FAB ionisation showed M+ at m/e=296.165 ±10 ppm (Calc. 296.168).

$^1$H NMR ($CDCl_3$) δ 0.80–0.95 (t, 3H), 1.40–1.55 (m, 2H), 2.10 (s, 3H), 2.45–3.20 (m, 8H), 3.70–3.90 (m, 2H), 3.90 (s, 3H), 4.2–4.3 (m, 1H), 6.40–6.55 (d, d, 2H), 7.0–7.1 (t, 1H).

EXAMPLE 15

Preparation of Intermediate 5-Hydroxy-3-(N-methylthioethyl-N-n-propylamino)-chroman A solution of 5-hydroxxy-3-(N-methylthioethyl-N-n-propylamino)chroman (166 mg, 0.56 mmol) in 48% aqueous HBr was heated at 120° C. for 30 min under nitrogen. The hydrobromic acid was evaporated and the residue was evaporated several times with absolute ethanol. Water was added and pH adjusted to 11 with 10% $Na_2CO_3$-solution. The aqueous solution was extracted with $CH_2CL_2$. The organic layer was separated, dried and the solvent was evaporated. The crude product was chromatographed ($SiO_2$) with light petroleum:ether (3:1) as eluant yielding 85 mg (54%) of 5-hydroxy-3-(N-methylthioethyl-N-n-propylamino)-chroman as an oil. The amine was converted to its hydrochloride with HCl-saturated ethanol. Evaporation and recrystallization gave the product as crystals.

m.p. 125°–130° C. $^1$H NMR ($CDCl_3$) δ 0.85–1.0 (t, 3H), 1.4–1.8 (m, 2H), 2.1 (s, 3H), 2.45–3.15 (m, 9H), 3.8–4.1 (m, br, 2H), 4.25–4.35 (m, 1H), 6.2–6.5 (d, 2H), 6.9–7.0 (t, 1H).

High resolution MS shows $M^+$ at m/e=281, 144±10 ppm (9). (Calc. 281 (145), 234 (100), 220 (89), 121 (31), 221 (15).

EXAMPLE 16

Preparation of 8-Bromo-3-(N-methylcyclopropyl-N-n-propylamino)-chroman

Commercially available 3-bromosalicylaldehyde (0.5 g; 2.5 mmol), di-n-butylammonium chloride (0.2 g; 1.2 mmol) and 2-nitroethanol (0.36 g; 4.0 mmol) were refluxed for 8 hours in i-pentylacetate with a Dean-Stark apparatus under nitrogen atmosphere. The solvent was evaporated and the product was dissolved in dichloromethane (15 ml) and cyanoborohydride (0.5 g; 8.1 mmol) in methanol (15 ml) was added. The mixture was stirred for 30 minutes at room temperature. Water was added and the mixture extracted with dichloromethane. The phase were separated and the organic layer was dried ($MgSO_4$). The solvent was evaporated yielding 400 mg (63%) of 8-bromo-3-nitrochroman as an oil.

8-Bromo-3-nitrochroman (400 mg; 1.55 mmol) was dissolved in glacial acetic acid (30 ml) and zinc dust (2 g) was added. The mixture was heated to 100° C. for 15 minutes. The zinc dust was filtered off and washed with dichloromethane. The solvent was evaporated and the remaining oil extracted with diluted hydrochloric acid/dichloromethane. The phases were separated and the pH of the water layer was adjusted to 11 with 2N NaOH. The water layer was extracted with dichloromethane. The phases were separated and the organic layer dried ($Na_2SO_4$). The solvent was evaporated yielding 214 mg (61%) of 8-bromo-3-aminochroman.

To a mixture of 8-bromo-3-aminochroman (200 mg; 0.9 mmol) in $CH_2Cl_2$ (25 ml) and 10% aqueous $Na_2CO_3$ (25 ml) was added propionyl chloride (400 mg; 2.2 mmol) and the mixture was stirred for 2 hours. The phases were separated and the organic layer was dried ($MgSO_4$). The solvent was evaporated and the crude amide was reduced with tetrabutylammonium borohydride (400 mg, 1.6 mmol) in a boiling (1:1)-mixture (50 ml) of dichloromethane and 1,2-dichloroethane overnight. The solution was extracted with water, dried ($Na_2SO_4$) and the solvent was evaporated yielding 140 mg (58%) of 8-bromo-3-(n-propylamino)chroman.

To a mixture of 8-bromo-3-(n-propylamino)chroman (120 mg; 0.5 mmol) in dichloromethane (20 ml) and 5% aqueous $Na_2CO_3$ (20 ml) was added cyclopropanecarbonyl chloride (300 mg; 3.5 mmol). The mixture was stirred for 2 hours, the phases were separated and the organic layer dried ($MgSO_4$). The solvent was evaporated and the crude amide was reduced with tetrabutylammonium borohydride (500 mg, 2.0 mmol) in a boiling (1:1)-mixture (50 ml) of dichloromethane and 1,2-dichloroethane for 24 hours. Hydrochloric acid (1M; 10 ml) was added and the phases were stirred for 1 hour at room temperature. pH was adjusted with 2M aqueous NaOH to 11 add the phases were separated. The organic layer was dried ($Na_2SO_4$) and the solvent evaporated yielding an oil, which was chromatographed ($SiO_2$) eluting with light petroleum:ether (3:1). The fractions containing pure product were pooled yielding 100 mg (61%) of 8-bromo-3-(N-methylcyclopropyl-N-n-propylamino)chroman. GC/MS showed $M^+$/M+2 at m/e=323 (11%)/325 (10% and the base peak pair m/e=294(110%)/296(98%).

EXAMPLE 17

Preparation of 6-Methylthio-3-(di-n-propylamino)chroman

A solution of 6-bromo-3-(di-n-propylamino)chroman (300 mg) in dry ether was treated with 1.6M n-BuLi in hexane (2.0 ml, 1.44 mmol) at 0° C. for 30 minutes under dry Ar-atmosphere. Dry, distilled dimethyl disulphide was added (0.5 ml, 5.8 mmol) and the mixture stirred for 2 hours at 0° C. The mixture was allowed to reach room temperature overnight, water was added and the phases were separated. The organic layer was washed with water, separated and dried ($Na_2SO_4$). The solvent was evaporated and the remaining oil chromatographed ($SiO_2$) with petroleum ether/ether (9:1) as eluant, yielding 57 mg of 6-methylthio-3-(di-n-propylamino)chroman as an oil. The amine was converted to its hydrochloride with HCl-saturated ethanol.

EXAMPLE 18

Preparation of Carbamoyl-Chromans

A solution of 6-bromo-3-(di-n-propylamino)chroman (900 mg) in dry ether was treated with 1.6M n-BuLi in hexane (0.9 ml, 1.44 mmol) at 0° C. for 2 hours under dry Ar-atmosphere. (The progress of the lithiation was checked by quenching small samples of the reaction mixture with dimethylformamide and running GC analysis of the product mixture formed.) The reaction mixture was poured into a $CO_2$-saturated solution (−78° C.) in dry ether, prepared by adding $CO_2(s)$ (20 g) to dry ether (50 ml). The mixture was allowed to stand overnight to reach room temperature and then water was added and the solvents were evaporated under reduced pressure. The residual mixture, 3-(di-n-propylamino)chromane-6-carbocxylic acid, was used in the next step without further purification.

The raw product from the previous reaction step was treated with $CH_2Cl_2$ (25 ml) and $SOCl_2$ (5 ml) and refluxed for 2 hours. The solvents were removed under reduced pressure and 3-(di-n-propylamino)chromane-6-carboxylic acid chloride was used in the syntheses described below without further purification.

A fraction of the raw acid chloride above (corresponding to 100 mg of pure product) was dissolved in $CH_2Cl_2$ (10 ml), and 10% $Na_2CO_3$ (10 ml) was added before the addition of benzylamine (1 ml). Workup was performed through extraction with 10% HCl, basification (10% NaOH) and $CH_2Cl_2$ extraction, yielding 150 mg of an oil which was chromatographed ($SiO_2$ and eluting with $CH_2Cl_2$:MeOH (45:1), yielding 20 mg of 3-(di-n-propylamino)-6-(benzyl)carbamoyl-chromane.

A fraction of the raw acid chloride above (corresponding to 100 mg of pure product) was dissolved in $CH_2Cl_2$ (10 ml), and 10% $Na_2CO_3$ (10 ml) was added before the addition of di-n-propylamine (3 ml). Workup was performed through extraction with 10% HCl, basification (20% NaOH) and $CH_2Cl_2$ extraction, yielding 150 mg of an oil which was chromatographed ($SiO_2$ and eluting with $CH_2Cl_2$:MeOH (9:1), yielding 15 mg of 3-(di-n-propylamino)-6-(di-n-propyl)carbamoyl-chromane.

A fraction of the raw acid chloride above (corresponding to 100 mg of pure product) was dissolved in $CH_2Cl_2$ (20 ml), and 10% $Na_2CO_3$ (20 ml) was added before the addition of saturated $NH_3$ in water (3 ml). Workup was performed through extraction with 10% HCl, basification (10% NaOH) and $CH_2Cl_2$ extraction, yielding 100 mg of an oil which was chromatographed ($SiO_2$ and eluting with $CH_2Cl_2$:MeOH (1:1), yielding 12 mg of 3-(di-n-propylamino)-6-carbamoyl-chromane.

EXAMPLE 19

Preparation of 6-Formamido-3-(di-n-propylamino)chromane and 6-hydroxymethyl-3-(di-n-propylaminochromane A solution of 6-bromo-3-(di-n-propylamino)chroman (190 mg) in dry ether was treated with 1.6M n-BuLi in hexane (2.0 ml, 1.44 mmol) at 0° C. for 30 minutes under dry Ar-atmosphere. Dry, dimethylformamide (1.5 ml) was added and the mixture stirred for 2 hours at 0° C. The mixture was allowed to reach room temperature overnight, water was added and the phases were separated. The organic layer was washed with water, separated and dried ($Na_2SO_4$). The solvent was evaporated and the remaining oil chromatographed ($SiO_2$) with petroleumether/ether; 3:1 as eluant, yielding 23 mg of the formamide and 21 mg of the hydroxymethyl analog as oils.

FORMULA CHART

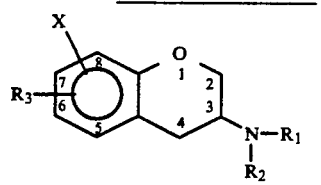

Formula I

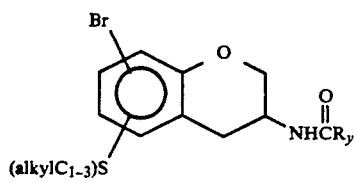

C-12

-continued
FORMULA CHART

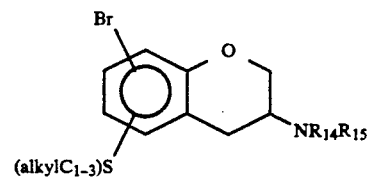

C-13

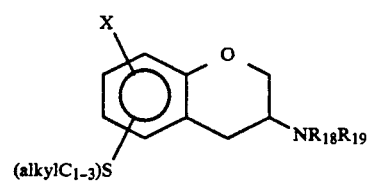

C-14

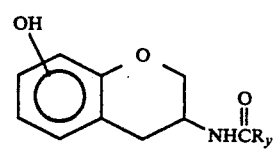

C-15

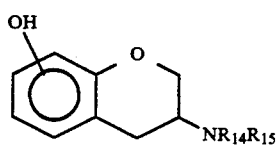

C-16

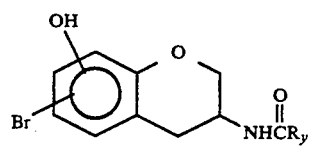

C-17

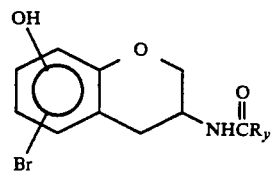

C-18

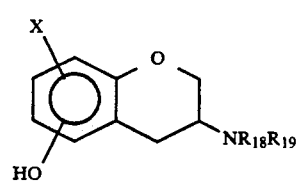

C-19

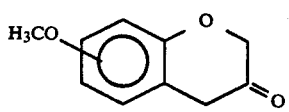

C-20

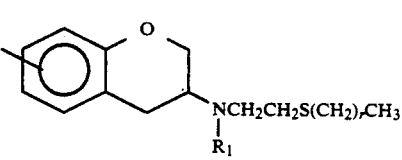

C-21

CHART 1

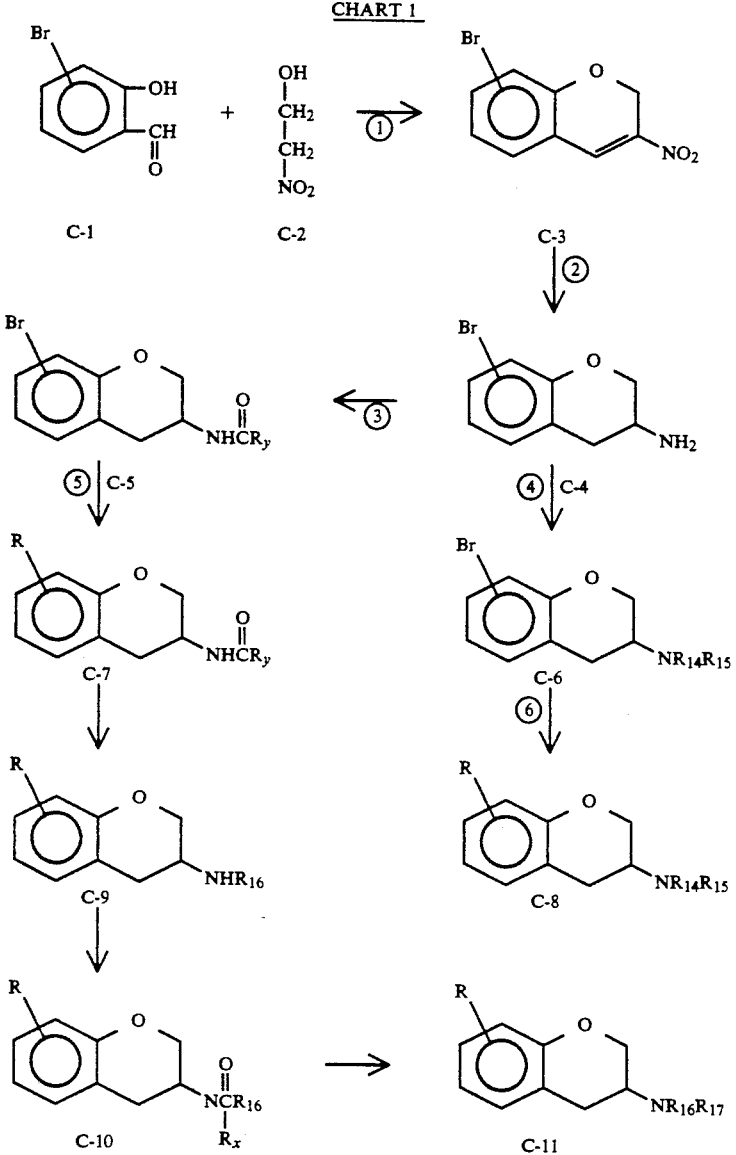

We claim:
1. A compound of the formula

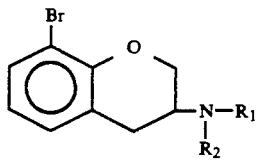

wherein:
$R_1$ is $C_{1-3}$ alkyl, cyclopropylmethyl, or cyclobutylmethyl;
$R_2$ is $C_{1-8}$ alkyl, $-(CH_2)_{1-3}-R_4$, $-CH_2-(C_{3-8}$ cycloalkyl$)$ or $-CH_2CH_2Z(CH_2)_{0-3}CH_3$; wherein $R_4$ is phenyl, phenyl substituted by one or two substituents selected from Cl, F, Br, $C_{1-3}$ alkoxy, $C_{1-3}$ alkyl, 2-thiophenyl, and 3-thiophenyl, and Z is $-O-$ or $-S-$;
or pharmaceutically acceptable salts thereof.
2. The compound of claim 1 wherein $R_1$ and $R_2$ are $C_{1-3}$ alkyl.
3. The compound of claim 2 wherein $R_1$ and $R_2$ are n-propyl.
4. The compound of claim 1 which is:
a) 8-Bromo-3-(di-n-propylamino)chroman, or
b) 8-Bromo-3-(N-cyclopropylmethyl-N-n-propylamino)chroman.

* * * * *